United States Patent
Matlock

(10) Patent No.: US 7,600,515 B2
(45) Date of Patent: Oct. 13, 2009

(54) TRACHEOSTOMY TUBE COMBINATION RADIAL SNAP AND BAYONET CANNULA CONNECTOR

(75) Inventor: George Matlock, Pleasanton, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 752 days.

(21) Appl. No.: 11/237,128

(22) Filed: Sep. 28, 2005

(65) Prior Publication Data

US 2007/0083262 A1    Apr. 12, 2007

(51) Int. Cl.
*A61M 11/00* (2006.01)
(52) U.S. Cl. .............................. 128/207.14; 128/207.15
(58) Field of Classification Search ............ 128/207.14, 128/207.15–207.17, 200.26
See application file for complete search history.

(56) References Cited

U.S. PATENT DOCUMENTS

| 2,786,469 | A |  | 3/1957 | Cohen |
| 3,169,529 | A |  | 2/1965 | Koenig |
| 4,573,460 | A |  | 3/1986 | Szachowicz et al. |
| 5,458,139 | A |  | 10/1995 | Pearl |
| 6,135,110 | A | * | 10/2000 | Roy ..................... 128/207.15 |
| 7,147,252 | B2 | * | 12/2006 | Teuscher et al. ............ 285/280 |
| 2007/0144526 | A1 | * | 6/2007 | Blom et al. ............ 128/207.16 |

* cited by examiner

*Primary Examiner*—Steven O Douglas
(74) *Attorney, Agent, or Firm*—Fletcher Yoder

(57) ABSTRACT

A medical device tube having extended retention tabs with notches therein for improved coupling of an inner cannula connector to an outer cannula connector. The medical device tube comprises an outer cannula connector having retention tabs on an outer cannula connector flange attached to the proximal end of an outer cannula. The retention tabs maintain the snap ears of the inner cannula connector when the inner cannula connector is rotated whereby the notches substantially hold the snap ears. The snap ears may further be positioned in notches in the outer cannula flange when the snap ears lock onto the outer cannula connector flange.

37 Claims, 6 Drawing Sheets

TRACHEOSTOMY TUBE COMBINATION RADIAL SNAP AND BAYONET CANNULA CONNECTOR

TECHNICAL FIELD

The present disclosure, according to one embodiment, relates to medical device tubes, e.g., tracheostomy tubes, used in medical applications, and more particularly, to improving the reliability of maintaining a secure attachment of an inner cannula to an outer cannula.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

A medical device tube may be comprised of an outer cannula (slender tube that may be inserted into a body cavity) attached to a head base connector. The head base connector and outer cannula are adapted for insertion of an inner cannula. One example of a medical device tube is a tracheostomy tube. The tracheostomy tube may be "L" shaped and the head base connector may be attached to a swivel neck plate/flange. The tracheostomy tube provides an artificial airway for access to the patient's airway for airway management. The tracheostomy tube may be introduced into a tracheotomy incision in the patient's neck that provides access to the trachea. The tracheostomy tube may be secured a swivel neck plate/flange that may be connected to a tracheostomy tube holder or neck strap, thus securing this artificial airway for spontaneous or mechanical ventilation of the patient.

The inner cannula may be inserted into the head base connector and outer cannula after the tracheostomy tube has been placed into the patient's trachea. This inner cannula typically includes a connector for quick removal of the inner cannula from the outer cannula, e.g., the inner cannula connector removably attaches to the head base connector, so that the inner cannula may be removed quickly if an obstruction, e.g., plug of mucus, sputum, etc., forms in the inner cannula. For example, a snap connector may be used for attaching the inner cannula to the outer cannula. A mechanical ventilator hose may be removably coupled to the inner cannula snap connector for assisting the patient in breathing. However, if the inner cannula is twisted during use, e.g., caused by movement of the ventilator hose connected thereto, the snap connector may disengage and allow the inner cannula to withdraw from the outer cannula.

SUMMARY

In previous medical device tube designs, a snap connector, e.g., a polypropylene material snap connector, having integral snap ears was used for attaching the inner cannula to the outer cannula head flange, with only the integral snap ears supplying retention between the inner and outer cannula connectors. Improving the reliability of attachment and continued attachment retention of the inner cannula connector to the outer cannula connector may be desired. Also, an added benefit would be to do so without having to change existing designs for the inner cannula snap connector, e.g., continued use of existing inner cannulas snap ear designs, but may also be utilized in any other or new medical device tube design.

According to a specific example embodiment of the present disclosure, a tracheostomy tube combination radial snap and bayonet cannula connector, includes an outer cannula snap flange; at least one retention tab having a first notch therein, wherein the at least one retention tab may be substantially parallel to a radial axis of the outer cannula snap flange; and the first notch receives and holds snap ears of an inner cannula connector when the snap ears are rotated into the first notch of the retention tab.

According to another specific example embodiment of the present disclosure, a medical device tube includes an outer cannula; an outer cannula snap flange coupled to the outer cannula; at least two retention tabs attached to the outer cannula snap flange, each of the at least two retention tabs having a first notch therein, wherein the at least two retention tabs are substantially parallel to a radial axis of the outer cannula snap flange; an inner cannula; and an inner cannula connector having snap ears, wherein the inner cannula connector may be coupled to the inner cannula, and the inner cannula may be adapted for insertion into the outer cannula, whereby the inner and outer cannulas may be substantially coaxially aligned; wherein the first notches receive and hold the snap ears of the inner cannula connector when the snap ears are rotated into the first notches of the at least two retention tabs.

According to yet another specific example embodiment of the present disclosure, a tracheostomy air passage system includes a tracheostomy tube comprising, an outer cannula; an outer cannula snap flange coupled to the outer cannula; at least two retention tabs attached to the outer cannula snap flange, each of the at least two retention tabs having a first notch therein, wherein the at least two retention tabs may be substantially parallel to a radial axis of the outer cannula snap flange; an inner cannula; and an inner cannula connector having snap ears, wherein the inner cannula connector may be coupled to the inner cannula, and the inner cannula may be adapted for insertion into the outer cannula, wherein the first notches receive and hold the snap ears of the inner cannula connector when the snap ears are rotated into the first notches of the at least two retention tabs, whereby the inner and outer cannulas may be substantially coaxially aligned; a ventilator hose coupled to the inner cannula connector; and a ventilator coupled to the ventilator hose.

BRIEF DESCRIPTION OF THE DRAWINGS

A more complete understanding of the present disclosure may be acquired by referring to the following description taken in conjunction with the accompanying drawings wherein.

Figure 1:
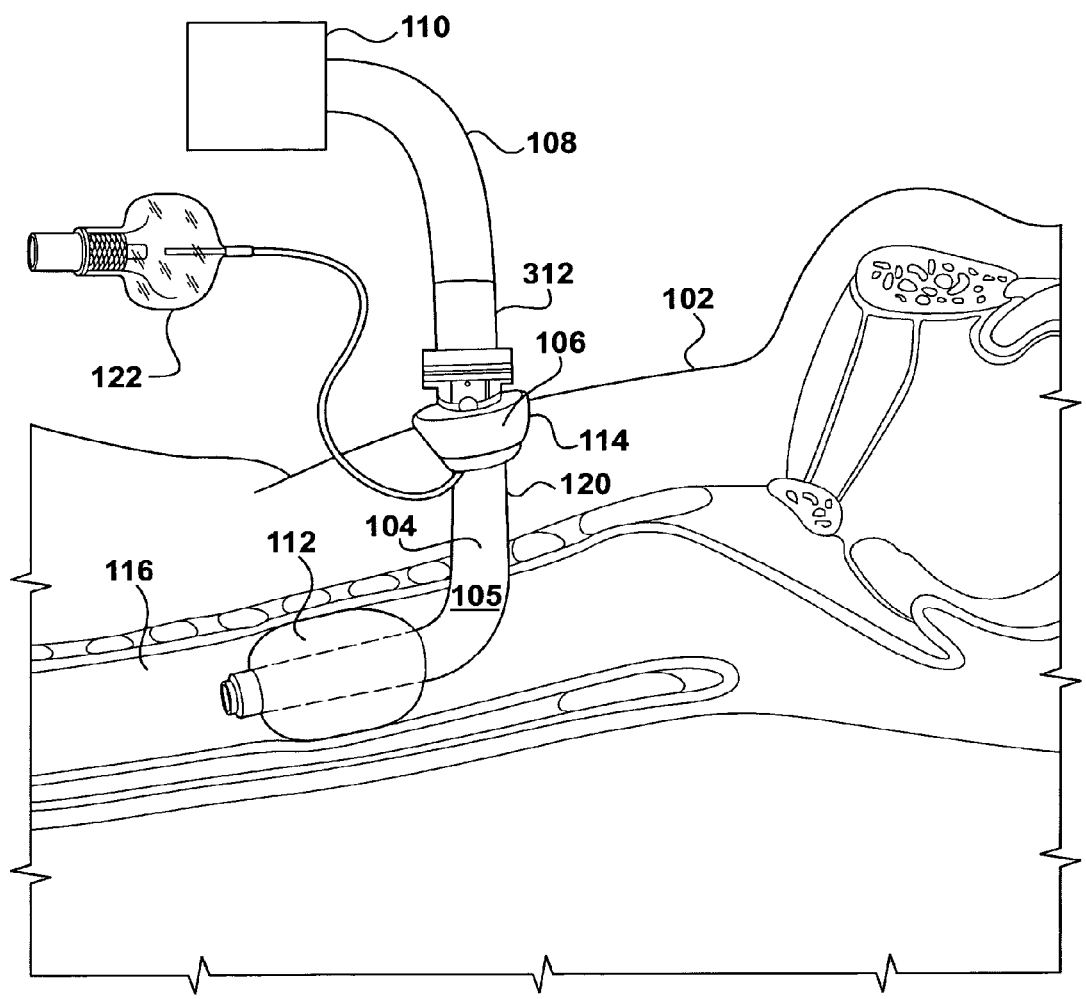
FIG. 1 is a schematic diagram of a patient ventilation system, according to a specific example embodiment of the present disclosure.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

Referring now to the drawings, the details of specific example embodiments are schematically illustrated. Like elements in the drawings will be represented by like numbers, and similar elements will be represented by like numbers with a different lower case letter suffix.

Referring to FIG. 1, depicted is a schematic diagram of a patient ventilation system, according to a specific example embodiment of the present disclosure. A patient 102 has a stoma 114 (opening) leading to his/her trachea 116 in which an outer cannula 104 is inserted. The outer cannula 104 may have a curved portion 105, e.g., L shaped. A neck flange 106 may be attached to the patient's 102 neck, e.g., by tape and/or straps, etc. (not shown). A ventilator hose 108 may couple a ventilator 110 to a ventilator hose coupling 312 of an inner cannula connector 306 (see FIGS. 4 and 6). The inner cannula connector 306 may be adapted for coupling to a speaking valve 307.

Optionally, an inflation collar 112 may be proximate to the outer wall of the outer cannula 104, and an inflation lumen 120 may be within the wall of the outer cannula 104 or proximate thereto. An air valve port 122 may be used in combination with the inflation lumen 120 and the inflation collar 112 for, when inflated, creating an air and/or liquid sealing function between the inflation collar 112 and the trachea 116 air passage. The inflation collar 112 may also position the outer cannula 104 in the trachea 116. More than one lumen may be in the wall of the cannula 104 and the additional lumens therein may be used for various other purposes. The inflation collar 112 may be inflated with a fluid, e.g., air, nitrogen, saline, water, etc.

Figure 2:
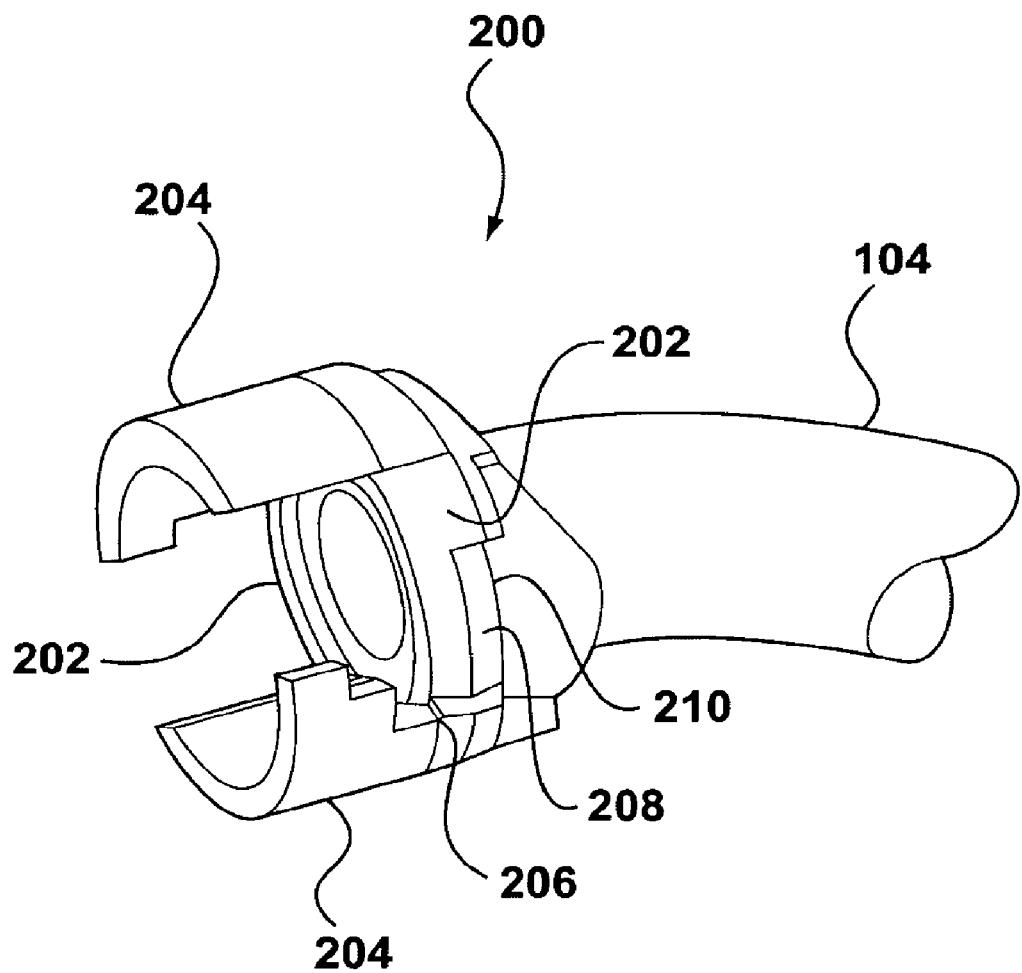
FIG. 2 is a schematic side view diagram of a radial snap and bayonet cannula connector attached to a proximal end of an outer cannula, according to a specific example embodiment of the present disclosure.

Referring to FIG. 2, depicted is a schematic side view diagram of a radial snap and bayonet outer cannula connector attached to a proximal end of an outer cannula, according to a specific example embodiment of the present disclosure. The radial snap and bayonet outer cannula connector, generally represented by the numeral 200, may comprise a snap flange 202 and retention tabs 204. The retention tabs 204 may be substantially parallel to a radial axis of the radial snap and bayonet outer cannula connector 200. The retention tabs 204 may further comprise first notches 206 in the retention tabs 204. These first notches 206 may be adapted for holding snap ears 308 (FIG. 3), e.g., bayonet style retention tabs. The snap flange 202 may further comprise second notches 208 adapted for further holding the snap ears 308 (FIGS. 3 and 4) once the snap ears 308 have engaged the snap flange 202. The second notches 208 may have slight bumps or locking protrusions 210 thereon for holding the snap ears 308 when the snap ears 308 are rotated thereover, e.g., locking indentations (not shown) on a face of the snap ears 308 slides over the locking protrusions 210. It is contemplated and within the scope of this disclosure that one or more retention tabs 204 may be used.

Figure 3:
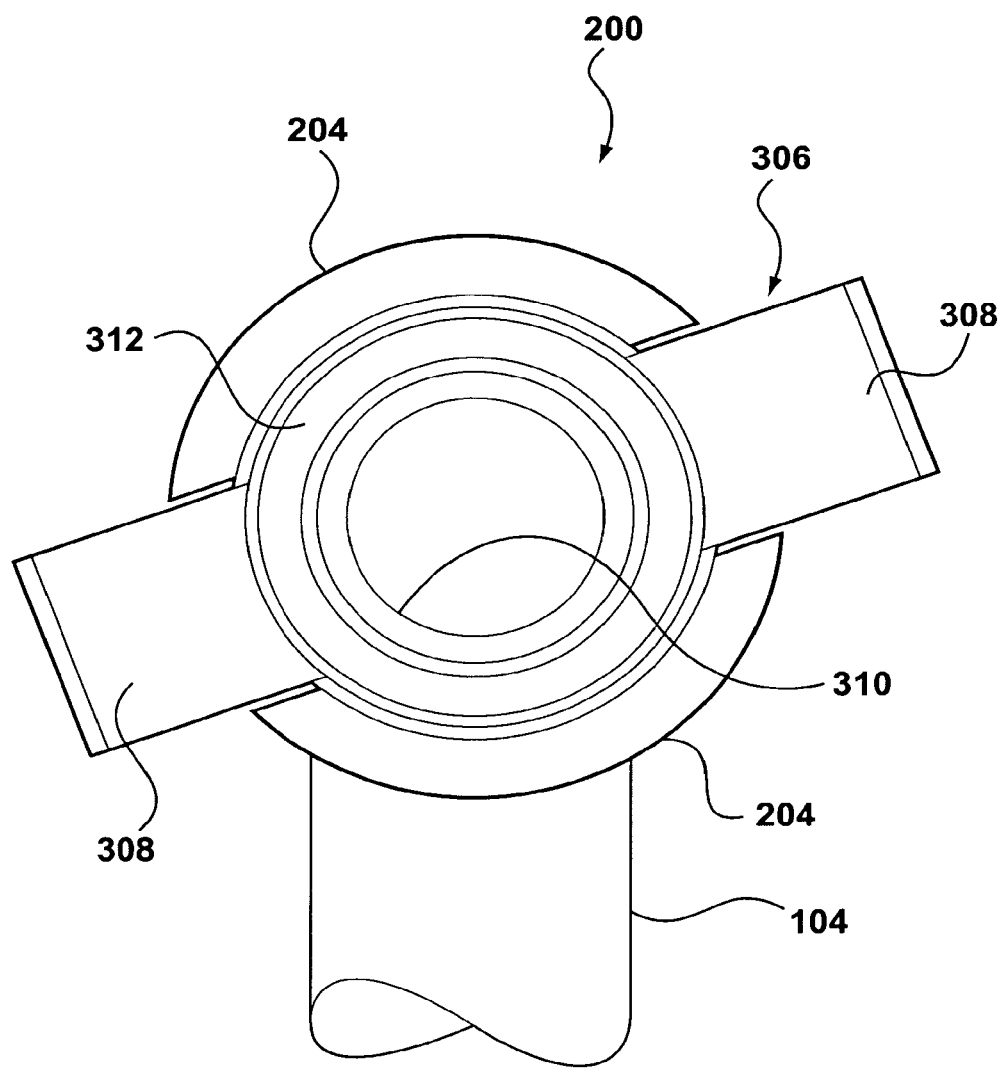
FIG. 3 is a schematic front view diagram of the radial snap and bayonet outer cannula connector illustrated in FIG. 2 and a mating inner cannula connector that is in an unlocked position with the radial snap and bayonet outer cannula connector.

Referring to FIG. 3, depicted is a schematic front view diagram of the radial snap and bayonet outer cannula connector 200, illustrated in FIG. 2, and a mating inner cannula connector, generally represented by the numeral 306, that is in an unlocked position with the radial snap and bayonet outer cannula connector 200. The inner cannula connector 306 may be attached to an inner cannula 310 and may comprise snap ears 308 and a ventilator hose coupling 312. The ventilator hose coupling 312 may be adapted for connection to the ventilator hose 108 (FIG. 1).

Figure 4:
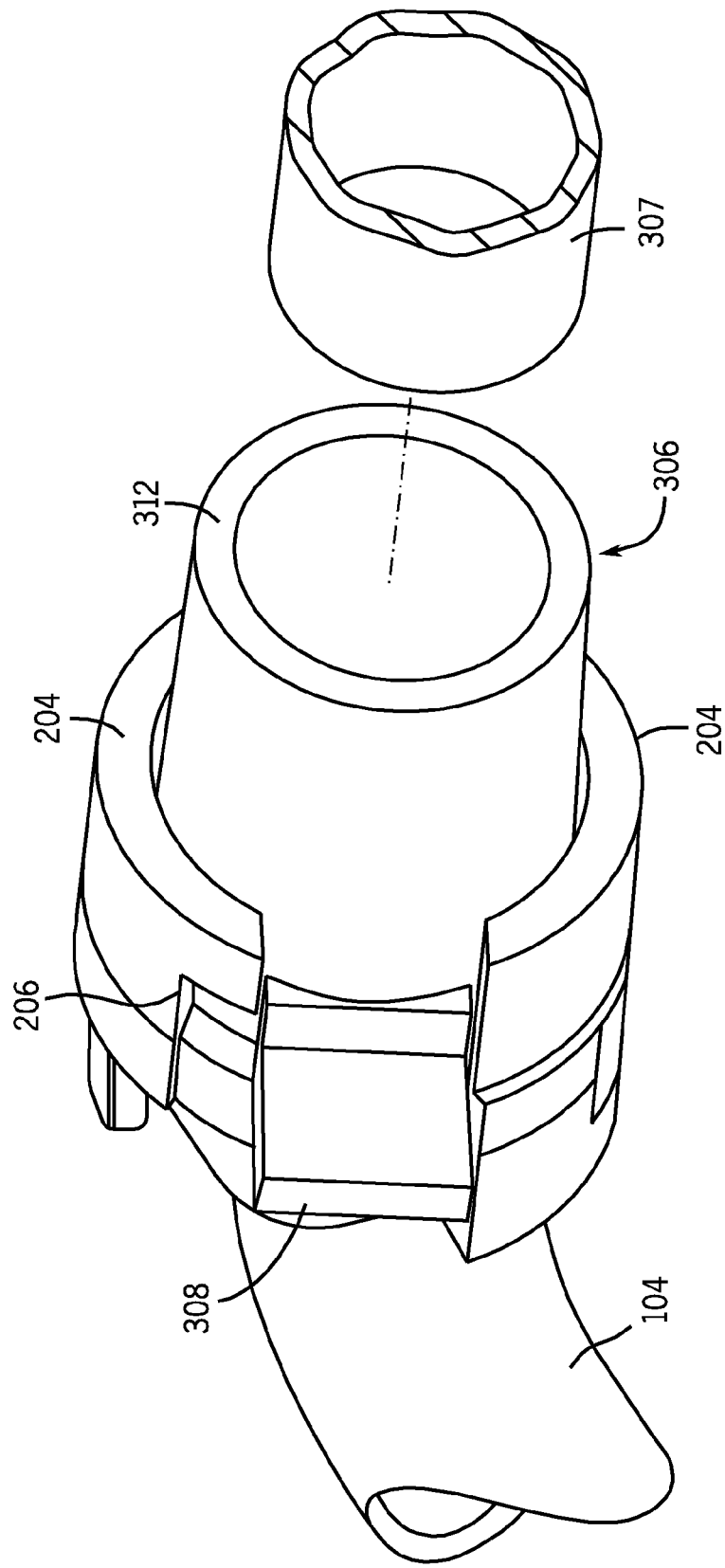
FIG. 4 is a schematic side view diagram of the radial snap and bayonet outer cannula connector and the mating inner cannula connector, illustrated in FIG. 3, in the unlocked position.

Referring to FIG. 4, depicted is a schematic side view diagram of the radial snap and bayonet outer cannula connector 200 and the mating inner cannula connector 306, illustrated in FIG. 3, in the unlocked position. The snap ears 308 may be adapted to fit between the retention tabs 204, twist into the first notches 206 and snap over the second notches 208, thereby securing the inner cannula connector 306 to the snap flange 202 of the radial snap and bayonet outer cannula connector 200.

Figure 5:
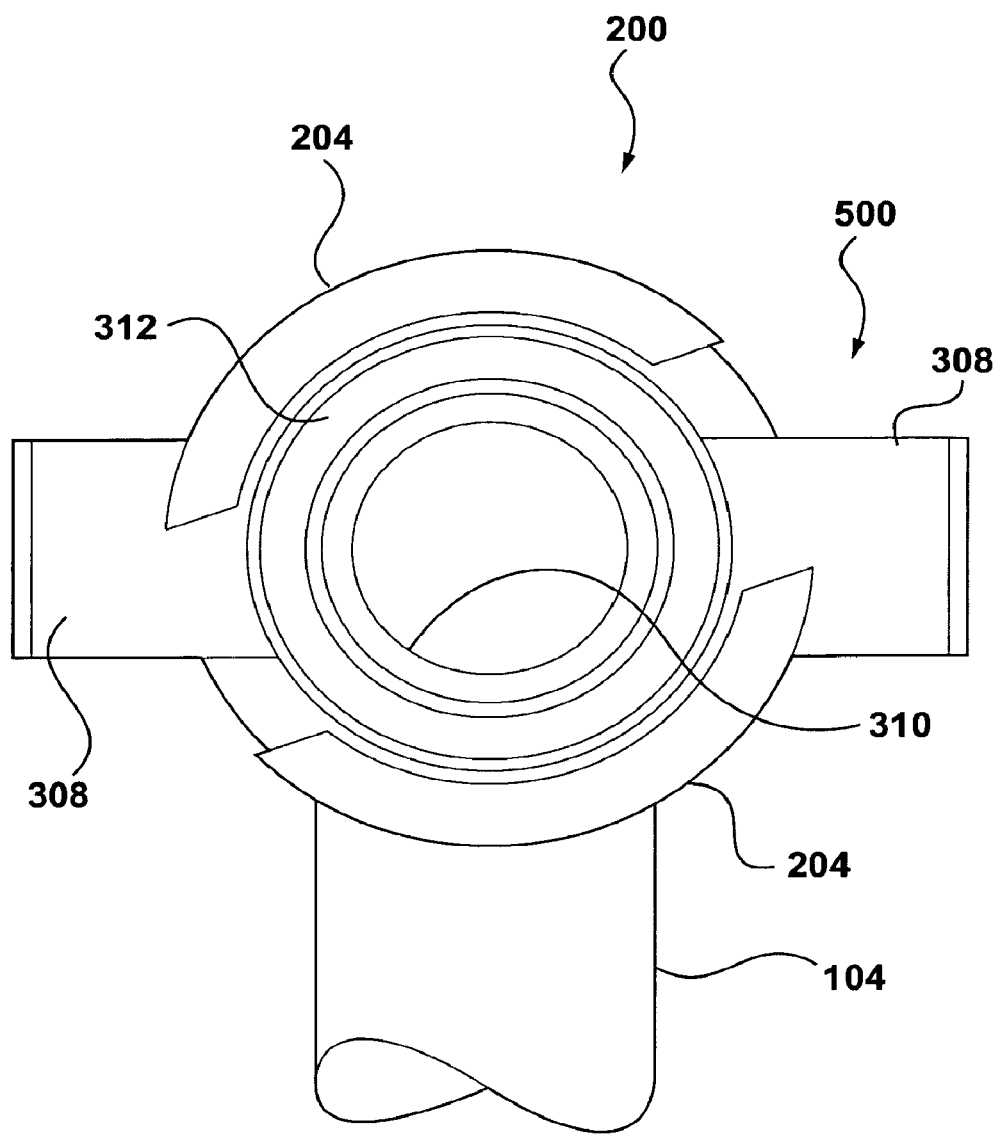
FIG. 5 is a schematic front view diagram of the radial snap and bayonet outer cannula connector illustrated in FIG. 2 and a mating inner cannula connector that is in a locked position with the radial snap and bayonet cannula connector.

Referring to FIG. 5, depicted is a schematic front view diagram of the radial snap and bayonet outer cannula connector 200, illustrated in FIG. 2, and the mating inner cannula connector 306 that is in a locked position with the radial snap and bayonet outer cannula connector 200.

Figure 6:
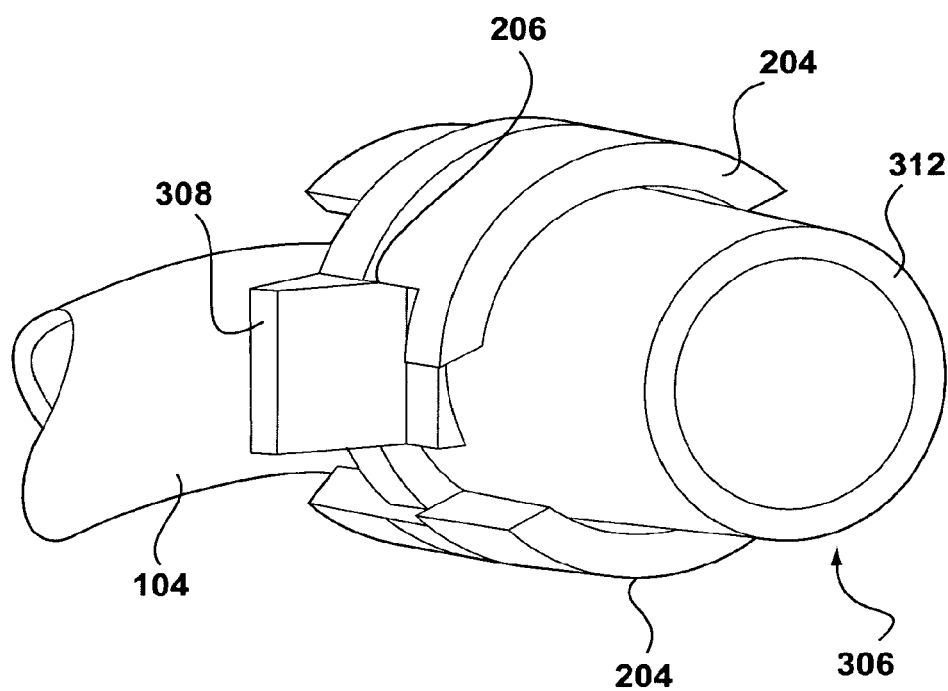
FIG. 6 is a schematic side view diagram of the radial snap and bayonet outer cannula connector and the mating inner cannula connector illustrated in FIG. 5 in the locked position.

Referring to FIG. 6, depicted is a schematic side view diagram of the radial snap and bayonet outer cannula connector 200 and the mating inner cannula connector 306, illustrated in FIG. 3, in the locked position. The snap ears 308 may be placed into the first notches 206 by turning in a rotational direction (polar rotation) 500 (FIG. 5) and thereafter may be snapped over the second notches 208 in the snap flange 202 (FIG. 2), thereby securing the inner cannula connector 306 to the snap flange 202 of the radial snap and bayonet outer cannula connector 200. Positioning the snap ears 308 between the retention tabs 204 may substantially prevent the snap ears 308 from undesirably disengaging, e.g., unlocking, from the snap flange 202 because of twisting and/or axial torque on the inner cannula connector 306. It is contemplated and within the scope of this disclosure that one or more retention tabs 204 may be used for substantially preventing the snap ears 308 from undesirably disengaging.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A tracheostomy tube combination radial snap and bayonet cannula connector, comprising:
    an outer cannula snap flange; and
    at least one retention tab associated with the outer cannula snap flange, the at least one retention tab having a first notch therein, wherein the at least one retention tab is substantially parallel to a radial axis of the outer cannula snap flange, and wherein the first notch receives and holds snap ears of an inner cannula connector when the snap ears are rotated into the first notch of the retention tab.

2. The tracheostomy tube combination radial snap and bayonet cannula connector according to claim 1, wherein the first notch comprises a plurality of first notches.

3. The tracheostomy tube combination radial snap and bayonet cannula connector according to claim 1, wherein the at least one retention tab comprises at least two retention tabs, each of the at least two retention tabs having one first notch.

4. The tracheostomy tube combination radial snap and bayonet cannula connector according to claim 1, wherein the snap ears lock onto the outer cannula snap flange.

5. The tracheostomy tube combination radial snap and bayonet cannula connector according to claim 4, comprising second notches in the outer cannula snap flange, wherein the second notches receive the snap ears when the snap ears lock onto the outer cannula snap flange.

6. The tracheostomy tube combination radial snap and bayonet cannula connector according to claim 5, wherein the second notches comprise locking protrusions thereon adapted for mating with locking indentations on a face of the snap ears.

7. The tracheostomy tube combination radial snap and bayonet cannula connector according to claim 1, wherein the inner cannula connector is coupled to a disposable inner cannula.

8. The tracheostomy tube combination radial snap and bayonet cannula connector according to claim 1, wherein the inner cannula connector is coupled to a reusable inner cannula.

9. The tracheostomy tube combination radial snap and bayonet cannula connector according to claim 1, wherein the inner cannula connector is a standard manufacture inner cannula connector.

10. The tracheostomy tube combination radial snap and bayonet cannula connector according to claim 1, wherein the outer cannula connector is coupled to an outer cannula.

11. The tracheostomy tube combination radial snap and bayonet cannula connector according to claim 10, wherein the outer cannula is adapted for insertion into a patient stoma.

12. The tracheostomy tube combination radial snap and bayonet cannula connector according to claim 1, wherein the at least one retention tab comprises two retention tabs having the first notches substantially parallel between the two retention tabs.

13. The tracheostomy tube combination radial snap and bayonet cannula connector according to claim 1, wherein the second notches and the snap ears are substantially in alignment when the snap ears have been rotated into the first notch of the at least one retention tab.

14. The tracheostomy tube combination radial snap and bayonet cannula connector according to claim 1, wherein the inner cannula connector is adapted for coupling to a ventilator hose.

15. The tracheostomy tube combination radial snap and bayonet cannula connector according to claim 1, wherein the inner cannula connector is adapted for coupling to a speaking valve.

16. The tracheostomy tube combination radial snap and bayonet cannula connector according to claim 1, comprising:
an inflation lumen; and
an inflation collar, wherein the inflation collar is positioned on an outside surface of an outer cannula and the inflation lumen is adapted for directing a fluid to the inflation collar for inflation thereof.

17. The tracheostomy tube combination radial snap and bayonet cannula connector according to claim 16, wherein the inflation collar is biased toward the distal end of the outer cannula.

18. A medical device tube, comprising:
an outer cannula;
an outer cannula snap flange coupled to the outer cannula;
at least two retention tabs attached to the outer cannula snap flange, each of the at least two retention tabs having a first notch therein, wherein the at least two retention tabs are substantially parallel to a radial axis of the outer cannula snap flange;
an inner cannula; and
an inner cannula connector having snap ears, wherein the inner cannula connector is coupled to the inner cannula, and the inner cannula is adapted for insertion into the outer cannula, whereby the inner and outer cannulas are substantially coaxially aligned;
wherein the first notches receive and hold the snap ears of the inner cannula connector when the snap ears are rotated into the first notches of the at least two retention tabs.

19. The medical device tube according to claim 18, wherein the snap ears lock onto the outer cannula snap flange.

20. The medical device tube according to claim 19, comprising second notches in the outer cannula snap flange, wherein the second notches receive the snap ears when the snap ears lock onto the outer cannula snap flange.

21. The medical device tube according to claim 20, wherein the second notches comprise locking protrusions thereon adapted for mating with locking indentations on a face of the snap ears.

22. The medical device tube according to claim 18, wherein the inner cannula connector is adapted for coupling to a speaking valve.

23. The medical device tube according to claim 18, comprising:
an inflation lumen; and
an inflation collar, wherein the inflation collar is positioned on an outside surface of the outer cannula and the inflation lumen is adapted for directing a fluid to the inflation collar for inflation thereof.

24. The medical apparatus according to claim 23, wherein the inflation collar is biased toward the distal end of the outer cannula.

25. The medical device tube according to claim 23, wherein the fluid is selected from the group consisting of air, nitrogen, saline, water, and combinations thereof.

26. The medical device tube according to claim 18, wherein the inner cannula is disposable.

27. The medical device tube according to claim 18, wherein the inner cannula is reusable.

28. A tracheostomy air passage system, said system comprising:
a tracheostomy tube comprising,
an outer cannula;
an outer cannula snap flange coupled to the outer cannula;
at least two retention tabs attached to the outer cannula snap flange, each of the at least two retention tabs having a first notch therein, wherein the at least two retention tabs are substantially parallel to a radial axis of the outer cannula snap flange;

an inner cannula; and an inner cannula connector having snap ears, wherein the inner cannula connector is coupled to the inner cannula, and the inner cannula is adapted for insertion into the outer cannula, wherein the first notches receive and hold the snap ears of the inner cannula connector when the snap ears are rotated into the first notches of the at least two retention tabs, whereby the inner and outer cannulas are substantially coaxially aligned;

a ventilator hose coupled to the inner cannula connector; and a ventilator coupled to the ventilator hose.

29. The tracheostomy air passage system according to claim 28, wherein the snap ears lock onto the outer cannula snap flange.

30. The tracheostomy air passage system according to claim 29, comprising second notches in the outer cannula snap flange, wherein the second notches receive the snap ears when the snap ears lock onto the outer cannula snap flange.

31. The tracheostomy air passage system according to claim 30, wherein the second notches further comprise locking protrusions thereon adapted for mating with locking indentations on a face of the snap ears.

32. The tracheostomy air passage system according to claim 28, wherein the inner cannula connector is a standard inner cannula connector.

33. The tracheostomy air passage system according to claim 28, wherein the inner cannula is disposable.

34. The tracheostomy air passage system according to claim 28, wherein the inner cannula is reusable.

35. The tracheostomy air passage system according to claim 28, comprising an inflation lumen; and an inflation collar, wherein the inflation collar is positioned on an outside surface of the outer cannula and the inflation lumen is adapted for directing a fluid to the inflation collar for inflation thereof so as to position and substantially seal the outer cannula in a patient trachea.

36. The tracheostomy air passage system according to claim 35, wherein the inflation collar is biased toward the distal end of the outer cannula.

37. The tracheostomy air passage system according to claim 28, wherein the inner cannula connector is adapted for coupling to a speaking valve.

* * * * *

UNITED STATES PATENT AND TRADEMARK OFFICE
CERTIFICATE OF CORRECTION

PATENT NO.       : 7,600,515 B2                                      Page 1 of 1
APPLICATION NO.  : 11/237128
DATED            : October 13, 2009
INVENTOR(S)      : George Matlock It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1050 days.

Signed and Sealed this

Fifth Day of October, 2010

David J. Kappos
*Director of the United States Patent and Trademark Office*